United States Patent [19]
Licata

[11] Patent Number: 6,102,919
[45] Date of Patent: *Aug. 15, 2000

[54] APPARATUS AND METHOD FOR REMOVING PARASITES

[76] Inventor: Joseph C. Licata, 109 Summit Dr., Manhasset, N.Y. 11030

[ * ] Notice: This patent issued on a continued prosecution application filed under 37 CFR 1.53(d), and is subject to the twenty year patent term provisions of 35 U.S.C. 154(a)(2).

[21] Appl. No.: 08/681,827

[22] Filed: Jul. 30, 1996

[51] Int. Cl.[7] ................................................. A61B 17/50
[52] U.S. Cl. ............................................ 606/131; 128/898
[58] Field of Search ............................ 227/63; 294/99.2; 254/18, 25, 28, 21; 606/131, 1; 128/898

[56] References Cited

U.S. PATENT DOCUMENTS

| | | | |
|---|---|---|---|
| 743,183 | 11/1903 | Miller | 254/25 |
| 1,615,125 | 1/1927 | Lespinasse . | |
| 1,835,443 | 12/1931 | Swoyer et al. . | |
| 3,680,834 | 8/1972 | Holloway . | |
| 4,039,140 | 8/1977 | Pulliam . | |
| 4,213,460 | 7/1980 | Weiner . | |
| 4,442,837 | 4/1984 | Keatley . | |
| 4,938,764 | 7/1990 | Glaberson | 606/131 |
| 4,976,718 | 12/1990 | Daniell | 606/131 |
| 5,116,347 | 5/1992 | Butler | 606/131 |
| 5,246,449 | 9/1993 | Webster | 606/131 |
| 5,276,306 | 1/1994 | Huffman . | |
| 5,374,274 | 12/1994 | Sproviero et al. | 606/131 |
| 5,380,339 | 1/1995 | Webster | 606/131 |
| 5,447,511 | 9/1995 | Gadd | 606/131 |

*Primary Examiner*—Glenn K. Dawson
*Attorney, Agent, or Firm*—Lowe Hauptman Gopstein Gilman & Berner

[57] ABSTRACT

A grooved portion of an apparatus is positioned between a tick and a host's skin. The grooved portion includes a tapered opening extending to a progressively narrowing groove, for guiding a tick towards a distal end thereof having force applying portions. The apparatus includes a fulcrum portion and, upon pivoting thereabout, force applying portions thereof adjacent the groove apply an extracting force to a tick from below, for complete extraction from the host without squeezing, crushing or severing body portions of the tick. The apparatus includes a concave spoon-like portion, with upstanding sidewalls, for retaining a tick after removal from the host.

3 Claims, 4 Drawing Sheets

APPARATUS AND METHOD FOR REMOVING PARASITES

TECHNICAL FIELD

This invention relates to devices for removing parasites, such as ticks, from humans and animals, and to methods for such removal. More specifically, the invention relates to devices for removal of such parasites, ticks and the like that do not apply squeezing force to the parasite or tick, thus avoiding introduction of infectious agents from the parasite to the host.

BACKGROUND ART

Much medical attention has recently been focused on tick-borne diseases occurring in human and animal hosts of parasites such as ticks (hereinafter ticks) due to organisms transmitted to the host by the tick. Such diseases are known to include Lyme disease, Ehrlichiosis, relapsing fever, Rocky Mountain Spotted Fever, Colorado Tick Fever, tick paralysis, tularemia and ricksettial diseases. Diseases transmitted to animals by ticks include Lyme disease, anaplasmosis, babesiosis, equine and St. Louis encephalitis, Q fever, and spirochetosis. Various of the above-listed illnesses may have devastating consequences if not promptly diagnosed or prevented.

Ticks, in particular, are an example of parasites which have an elongated mouth projecting from a head portion attached to their bodies. Upon attachment of a tick to a host, whether animal or human, typically there exists a window of opportunity of several hours before infectious agents are transmitted from the tick into the host. Accordingly, prompt and complete removal of a tick during this window of opportunity greatly reduces risk of infection of the host.

To be effective, such removal must not squeeze or crush the body of the tick, or otherwise irritate the tick, in order to avoid the possibility of regurgitation or injection by the tick of its infectious agents into the host. Moreover, any mouth parts of the tick which may have been imbedded in the host's skin should also be removed, along with any adhesive cement secreted by the tick, in order further to minimize the possibility of infection.

It has been noted that some sufferers of tick-borne diseases contracted the illnesses because of improper removal of the tick, rather than by the tick bite itself. Accordingly, there is a need in the prior art to provide method and apparatus for effective removal of ticks and other parasites without crushing, twisting or squeezing the parasite body, and without severing (or otherwise damaging) portions of the parasite's body.

Numerous prior art devices have been advanced for tick removal. Some such devices apply heat or chemicals to the attached tick. However, application of heat, irritating or poisonous chemicals may irritate the tick and cause the tick to inject its viral or bacterial infectants into the host.

Other tick removal devices often apply a squeezing motion which, if applied to the body of the tick, may result in the undesirable consequences hereinabove mentioned. Thus, commonly utilized tweezers, forceps and tweezers- or forceps-like devices carry the risk of stimulating the tick to infect the host while removing portions of the tick's body from the host. Similarly, rotation of the tick to dislodge the tick from the host is likely to sever the tick's body from its head which itself would remain buried in the host and act as a source of infectious agents for the host.

Accordingly, the prior art has not provided a device capable of safe and complete removal of a tick from its host.

DISCLOSURE OF THE INVENTION

It is accordingly an object of the present invention to overcome the difficulties of the prior art and to provide apparatus and method for complete removal of a tick or other parasite from its host, while avoiding squeezing, crushing, or separating body components of the parasite.

It is a more particular object of the invention to provide an apparatus including a handle, a fulcrum, and a forked portion for engaging a parasite and for removing the parasite by pivoting the apparatus about the fulcrum when resting on the host's skin.

Yet another object of the invention is to provide an apparatus for removing a parasite, which includes a tapered opening for guiding the parasite to a section of the apparatus applying an extracting force thereto.

Still another object of the invention is to provide an apparatus for removing a parasite, having a rounded fulcrum for smoothly resting and pivoting on a host's skin, and including a concave portion on an opposing surface of the fulcrum for receiving the parasite therein.

It is still another object of the invention to provide an apparatus for removing a parasite in which a concave portion receiving the parasite includes up-raised walls at lateral edges thereof to retain the parasite after extraction.

It is another object of the invention to provide a method for extracting parasites from a host's skin by placing, between the parasite and the host's skin, an apparatus having an opening for receiving the parasite, and by using portions of the apparatus adjacent the opening to apply force away from the host's skin.

It is a more particular object of the invention to provide a method for extracting a parasite by sliding a grooved apparatus between the parasite and the host's skin, in which a groove in the apparatus is dimensioned to be smaller than a portion of the parasite protruding from the host's skin, thereby to entrap the protruding portion of the parasite in the apparatus.

It is a more specific object of the invention to remove a parasite by pivoting an apparatus about its fulcrum, thereby to push the parasite away from the host's skin using portions of the apparatus adjacent an opening used to entrap the parasite therein.

In accordance with the invention, there is thus provided an improved parasite removing apparatus for removing a parasite from a host by application of an extracting force directly thereto for withdrawing the parasite from the host. The inventive apparatus is particularly useful for removing a parasite having at least first and second body portions wherein the first body portion has a first, narrow, cross sectional dimension and the second body portion has a second, wide, cross sectional dimension larger than the first cross sectional dimension, where the first, narrower, body portion of the parasite is embedded in the host's skin.

The improved apparatus according to the invention comprises: a handle; a forked portion dimensioned for engaging the second (larger) body portion of the parasite; and a fulcrum connected to the handle and to the forked portion. In accordance with the invention embodied by such a structure, the forked portion, engaged with the second body portion of the parasite, is moved away from the host's skin to remove the parasite therefrom by resting the fulcrum on the host's skin and pivoting the apparatus about the fulcrum.

The fulcrum may include a rounded surface for resting on the host's skin and smoothly rotating the apparatus thereabout.

Preferably, the parasite removing apparatus includes a concave, spoon-like portion for receiving the parasite, the concave portion and the rounded surface being on opposing surfaces of the apparatus. Moreover, the apparatus may be structured to include upraised walls at edges of the concave portion, for retaining the parasite in the concave portion both during and after removal Preferably, the forked portion includes a tapered opening, having a wide port which tapers to a grooved portion which has a dimension smaller than the second cross sectional dimension, for guiding the parasite to a section of the apparatus which applies an extraction force substantially directly to the parasite.

In such a structure, the grooved portion may include a progressively narrow channel for securely engaging the second body portion of the parasite.

In accordance with one aspect of the invention, the handle is longer than the forked portion to provide mechanical advantage when pivoting the apparatus to remove the parasite. Moreover, the handle may be curved to form a generally S-shaped configuration with the fulcrum, thereby enabling the handle to be pivoted about a finger of a user applying the apparatus to the host and simplifying the removal process.

In accordance with another feature of the invention, there is provided a method for extracting a parasite embedded in a host's skin, including the steps of: placing an apparatus, having an opening for receiving the parasite, between the parasite and the host's skin to entrap the parasite; and applying to the parasite force in a direction pointed away from the host's skin to the parasite by portions of the apparatus adjacent the opening.

Preferably, the apparatus is placed between the parasite and the host's skin by sliding a grooved apparatus between the parasite and the host's skin, the groove being dimensioned to be smaller than a dimension of a portion of the parasite protruding from the host's skin, thereby entrapping the protruding portion of the parasite in the apparatus.

Moreover, the extracting force is preferably applied to the parasite by placing the fulcrum of the apparatus on the host's skin and pivotally rotating the apparatus about the fulcrum, so as to push the parasite away from the host's skin using portions of the apparatus adjacent the groove or other opening.

These and other objects, features and advantages of the present invention will become readily apparent to those skilled in the art from the following description and drawings, wherein there is shown and described a preferred embodiment of the invention, simply by way of illustration and not of limitation of one of the best modes (and alternative embodiments) suited to carry out the invention. The invention itself is set forth in the claims appended hereto. As will be realized upon examination of the specification and drawings and from practice of the same, the present invention is capable of still other, different, embodiments and its several details are capable of modifications in various obvious aspects, all without departing from the scope of the invention as recited in the claims. Accordingly, the drawings and the descriptions provided herein are to be regarded as illustrative in nature and not as restrictive of the invention.

BRIEF DESCRIPTION OF THE DRAWING

The accompanying drawings, incorporated into and forming a part of the specification, illustrate several aspects of a preferred embodiment of the present invention and, together with the description, serve to explain the principles of the invention.

In the drawings.

BEST MODE FOR CARRYING OUT THE INVENTION

Figures 1, 2, 3:
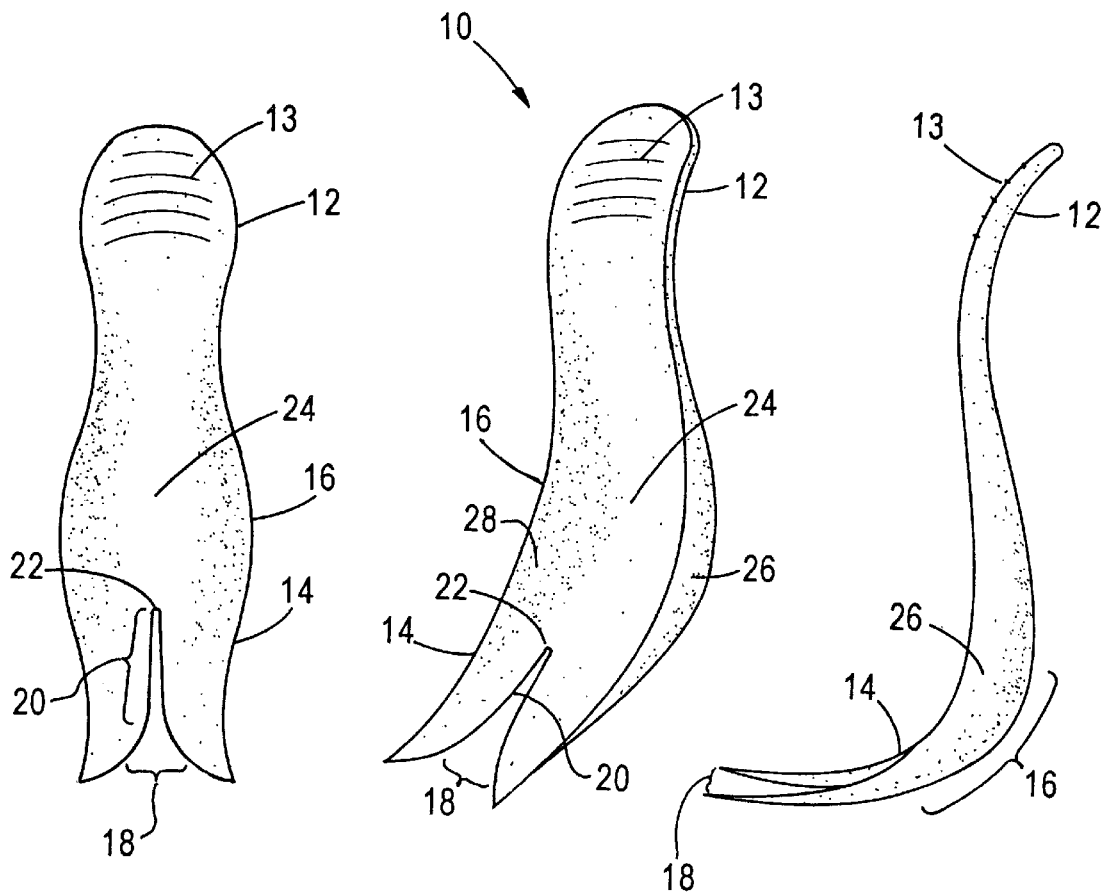
FIG. 1 is a perspective view of a preferred embodiment of a tick removing apparatus in accordance with the invention.
FIG. 2 is a front elevation view of the preferred embodiment of the invention shown in FIG. 1.
FIG. 3 is a side elevation view of the preferred embodiment of the invention shown in FIG. 1.

Referring now to the drawings, in FIG. 1 there is shown in perspective a preferred embodiment of a parasite removing apparatus in accordance with the invention, which is particularly well suited for removal of ticks from the skin of a host, whether human or animal. Other views of the inventive apparatus, specifically front elevation and side elevation views thereof, are shown in FIGS. 2 and 3, each of which should be referenced in consideration of the following description.

As shown in the drawing figures, the inventive apparatus, which is generally labelled by the reference numeral 10, includes a handle 12, a forked portion 14, and a fulcrum portion 16 which is connected to the handle and to the forked portion 14.

Preferably, fulcrum portion 16 has a generally rounded shape as illustrated in FIGS. 1–3, although it should be appreciated that the invention may be practiced with apparatus having a flat resting plane instead of a curved or rounded shape as shown, or with an apparatus having a pivot axis or a pivot point. Moreover, for ease in grasping the inventive apparatus, at least a portion of the handle 12 may be knurled or grooved, as illustrated by grooves 13 in the figures.

Forked portion 14 includes a port, or opening, 18, which tapers from a wide inlet portion to a narrower portion 20, shown in the drawing figures as having a progressively narrowing groove therein. Although the groove of portion 20 may have a substantially fixed width, it will be appreciated from the following description that certain advantages accrue to the inventive apparatus by providing the progressively narrowing shape and structure shown in FIGS. 1–3.

Moreover, the progressively narrowing structure of the groove in the narrow portion 20 of opening 18 is illustrated in the drawings as having a curved shape. However, it should be understood that the edges of the groove may be linear or piecewise linear in shape, and may provide a linear, rather than curved, narrowing of the groove width with distance from opening 18. Whether the groove of portion 20 is curved or linear, however, at its distal end 22 (furthest removed from opening 18) there is preferably provided a smoothed, rounded, narrow end.

In general, a central portion of the apparatus, shown at 24, is slightly wider than the handle 12. Indeed, as may be best appreciated from FIGS. 1 and 3, central portion 24 is preferably slightly hollowed or concave, forming a spoon-like structure. To further emphasize this structural feature of the inventive apparatus, there are provided laterally displaced raised side-walls 26 and 28, one on each side of the concave central portion 24.

It should be appreciated that the inventive apparatus may be made of almost any material which would have sufficient rigidity to withstand relatively minimal forces applied for withdrawal of a parasite in accordance with the method illustrated in FIGS. 6a–7c, described in detail hereinbelow. Thus, while an example of the invention was prepared from aluminum because of the ease of working with that material, almost any metal, from steel to copper to tin could be used. Alternatively, the apparatus could also be molded of plastic.

Figure 4:
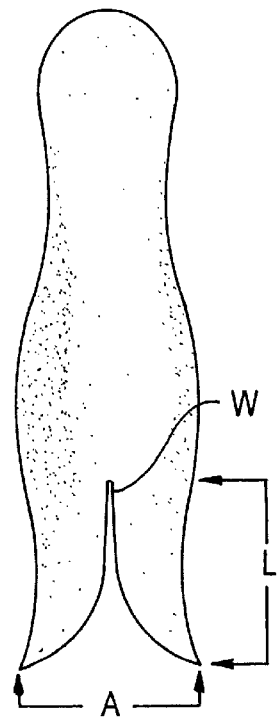
FIG. 4 shows structural dimensions of one illustrative example of the embodiment shown in FIG. 2.
Figure 5:
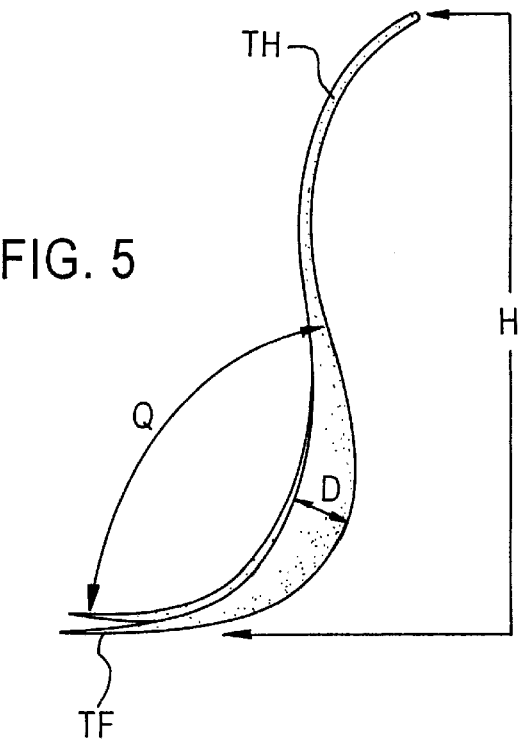
FIG. 5 shows additional dimensions of an illustrative example of the embodiment shown in FIG. 3.
Figure 6A:
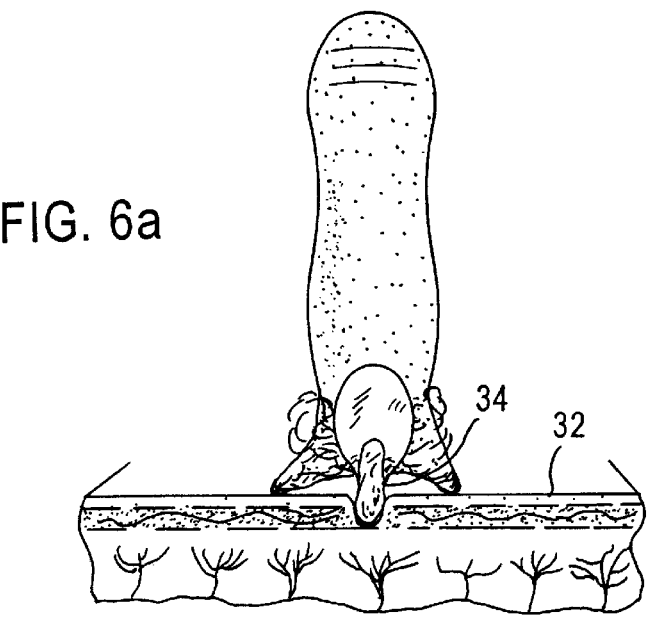
FIGS. 6a–6c are front views illustrating a method of removing a tick from a host in accordance with the invention, using the preferred embodiment of the inventive apparatus.
Figure 6B:
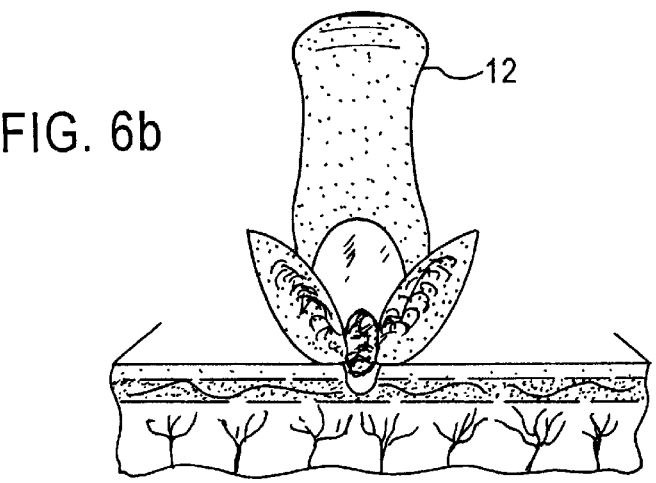
Figure 6C:
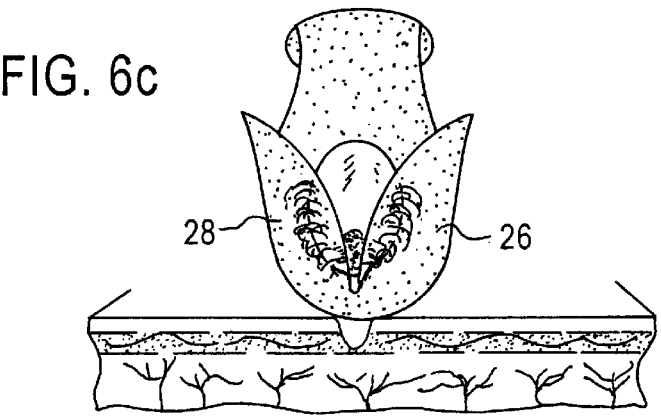

According to one example of the inventive apparatus, shown in FIGS. 4 and 5, the following dimensions were found to be useful in removal of an embedded tick. Opening 18 of FIG. 2, which is preferably smooth to avoid severing body parts of a tick and which is tapered to guide the tick to the grooved portion 20, is large enough to accept the head and mouth parts of the tick. By providing a varying radius of curvature both for the opening port and for the groove, the device is given an advantageous capability of accepting body parts of varying sizes, for different ticks or parasites.

Of course, a plurality of fixed-dimension devices may be provided in accordance with the inventive concept, each capable of accepting, or capturing, a particular size or range of sizes of ticks. Thus, the curvature from the opening 18 to the groove, i.e., the degree of taper, may be reduced and the width of the groove may be less varied, to provide simpler manufacture upon reducing the size range of ticks which may be captured and removed by each such device.

While the dimension of the opening A shown in FIG. 4 may illustratively be in the range of 0.2 to 0.4 inches, in the example shown in FIG. 4 opening A was preferably 0.3 inches in width. Moreover, while the length L of the groove from opening A to its distal end may illustratively be in the range of 0.3 to 0.6 inches, in the example of FIG. 4 the length L was preferably 0.45 inches. Additionally, the width W of the groove at its distal end preferably is as narrow as possible, in consonance with the material of the apparatus and expenses of manufacture thereof, while at the same time avoiding too narrow a dimension which may result in severance of body parts of the tick.

Thus, the end width, and radius of curvature, of the groove may be in the range of 0.005 to 0.015 inches. In the example shown in FIG. 4, which was made of a strip of aluminum, the minimum width of the groove at its distal end was preferably 0.01 inch.

The example of FIG. 4 has a height H (shown in FIG. 5) which may be in the range 1.5 to 2.5 inches. In the example shown in FIG. 5, height H was preferably 2.0 inches. Moreover, the thickness of the inventive apparatus should be thin enough to permit placement of the forked portion between the host's skin and the tick embedded therein, while being thick enough to provide sufficient rigidity and strength as to avoid bending when applied. Thus, at the proximal (forward) end of the forked portion 14, for an apparatus formed of aluminum, a thickness TF may be in the range of 0.0075 to 0.02 inches, with a preferred thickness of 0.01 inch. On the other hand, to assure that handle 12 may be easily grasped by the user, the handle thickness TH may thus be in the range of 0.01 to 0.10 inches and, in the example made of an aluminum strip and illustrated in FIG. 5, the thickness TH was preferably 0.03 inches.

In order to retain an extracted tick after removal from the host, side-walls 26 and 28 are structured to result in a depth D of the spoon-like structure which corresponds to the size of the ticks being extracted. In general, depth D may be in the range of 0.1 to 0.3 inches, with a preferred value of approximately 0.2 inches as shown in FIG. 5.

The angle Q between the central portion and the forked portion of the apparatus is selected to provide an appropriate mechanical advantage when pivoting the apparatus about its fulcrum, as well as to permit the user to manipulate the apparatus in a limited operating space. Thus, while angle Q may be in a range of 65 to 90 degrees, for example, the preferred angle is approximately 75 degrees.

A method of operation of the invention will now be described with reference to FIGS. 6a–6c and 7a–7c.

Figure 7A:
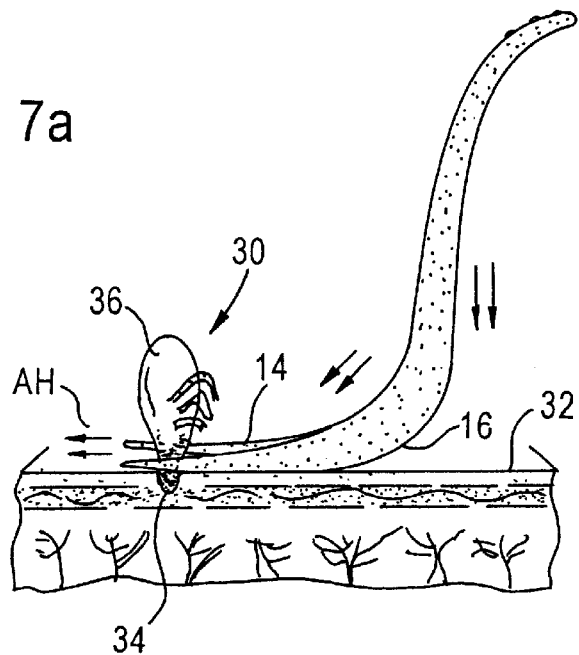
FIGS. 7a–7c are side views corresponding to the front views of FIGS. 6a–6c to illustrate the method of removing a tick from a host in accordance with the invention.

As shown therein, and as particularly indicated by the horizontal arrows AH of FIG. 7a, in operation the forked portion 14 is slid between a tick 30 and the skin 32 of the host.

Tick 30 has two body portions. A first portion, shown as a narrow head portion 34 including an elongated mouth, is embedded in the host's skin 32. A second, wider, body portion 36 extends from the first portion 34. By sliding forked portion 14 between the body portion of tick 30 and the host's skin 32, at some point during the sliding operation the progressively narrowing grooved portion 20 is brought in contact with the second portion 36 of the tick. Depending on the size of the tick and the groove, preferably such contact takes place when the tick is at the distal end of the groove.

Figure 7B:
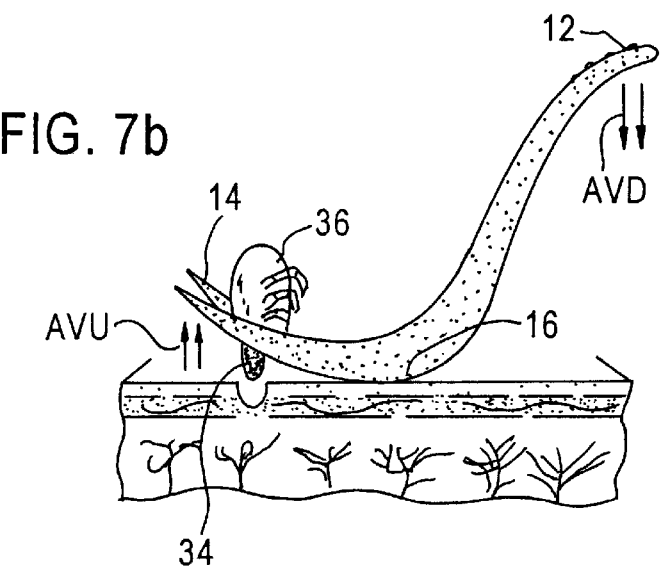

At that point, handle 12 is pushed downwardly, as indicated by downwardly pointing vertical arrows AVD in FIG. 7b, thus pivoting the apparatus about fulcrum portion 16. Such pivoting motion results in an upward vertical movement of the forked portion 14 of the apparatus, as indicated by upwardly pointing vertical arrows AVU in FIG. 7b. This upward vertical movement of forked portion 14 results in direct application, by portions of the apparatus adjacent the groove, of a substantially vertical force to the large body portion 36 of the tick engaged by the apparatus.

That is, the invention does not squeeze the tick's body or grab it from above but, instead, applies to the tick a separating force from below, directed away from the host's skin, in order to extract the elongated mouth and head of the tick from the host, without crushing or severing any body parts or otherwise disturbing the tick in a manner which would cause the tick to regurgitate and/or inject infectious viral or bacterial material into the host. With the tick's head embedded in the host's skin, upward pivoting of the forked portion 14 thus entraps the tick against the forked portion, and applies an extracting force thereto.

In view of the pivoting action of the invention, it will be appreciated that a mechanical advantage is gained for the user when the length of the handle 12 (e.g., the distance between the fulcrum portion 16 and the end of handle 12) is made greater than the length of the forked portion (e.g., the distance between the fulcrum portion 16 and the proximal end of the groove at opening 18).

Moreover, by providing an S-shaped curvature to the handle and fulcrum portion, it will be appreciated that the curved portion of handle 12 may be rested on a user's index or middle finger below the handle, for example, while downward force may be applied to the handle from above by the user's thumb, permitting rotation of the apparatus about the user's finger as well as pivoting of the apparatus about the fulcrum portion.

Figure 7C:
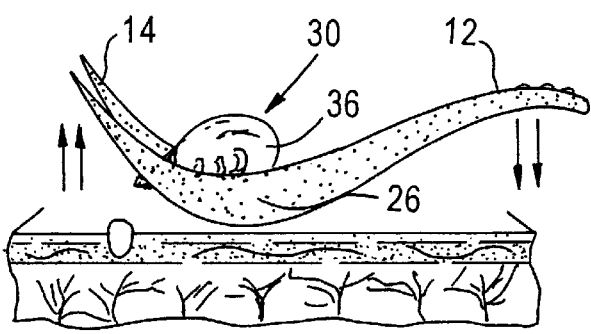

As shown in FIG. 7c, upon sufficient pivoting of the inventive apparatus, tick 30 is extracted from the host. The generally concave structure of the apparatus, at a surface portion thereof generally opposing the fulcrum portion 16, together with the upstanding walls 26 and 28 provided therein, retains the tick after withdrawal by the apparatus, and permits easy removal and disposal of the tick from the apparatus once withdrawn from the host.

While the extracting force is illustrated in FIGS. 6a–7c as being applied directly to the tick, it will be appreciated that the extracting force may be applied to the tick through an intervening medium, whether for hygienic or other reasons. As noted, the extracting force is generally directed away from the host's skin, and is preferably applied in a direction substantially perpendicular to the skin, to remove the parasite therefrom. Of course, the actual direction of the applied force will depend on the distance to which the tick is inserted in grooved portion 20 before the user pivots the apparatus about fulcrum 16, the height of the large body portion 36 of the tick above the host's skin when such pivoting takes place, the curvature of the fulcrum and the forked portion, and other factors which will be understood by one of ordinary skill in the art.

The foregoing description of the preferred embodiment of the invention has been presented for purposes of illustration and description. It is not intended to be exhaustive or to limit the invention to the precise forms disclosed, since many modifications or variations thereof are possible in light of the above teaching. All such modifications and variations are within the scope of the invention. The embodiments described herein were chosen and described in order best to explain the principles of the invention and its practical application, thereby to enable others skilled in the art to utilize the invention in various embodiments and with various modifications as are suited to the particular use contemplated therefor. It is intended that the scope of the invention be defined by the claims appended hereto, when interpreted in accordance with the full breadth to which they are legally and equitably entitled.

What is claimed is:

1. A method for extracting a parasite embedded in a host's skin by using a spoon-like appparatus, comprising the steps of:

placing on the host's skin and between the host's skin and the parasite a rounded convex fulcrum portion at one surface of a front spoon portion of the spoon-like apparatus having a curved handle projecting rearwardly from the spoon portion and a forked portion projecting forwardly from the spoon portion, the forked portion having an opening dimensioned for engaging the second body portion of the parasite, the spoon portion being concave on an upper surface thereof opposite the surface including the convex fulcrum portion therein;

using portions of the forked portion adjacent the opening to apply force away from the host's skin to the parasite and to extract the parasite towards a rear of the apparatus by pivotally rotating the spoon-like apparatus about the fulcrum to push the parasite away from the host's skin using the portions of the apparatus adjacent the opening; and retaining the extracted parasite in the spoon portion rearwardly of the opening of the forked portion.

2. The method of claim 1, wherein said step of placing a rounded convex fulcrum portion comprises sliding the portions adjacent the opening of the forked portion between the parasite and the host's skin, the opening having a groove dimensioned to be smaller than a dimension of a portion of the parasite protruding from the host's skin, thereby entrapping the protruding portion of the parasite in the spoon portion of the spoon-like apparatus.

3. The method of claim 1, wherein said step of pivotally rotating the spoon-like apparatus comprises applying a force to a distal portion of the curved handle thereof toward the host's skin, thereby causing the spoon-like apparatus to pivotally rotate about the fulcrum to push the parasite away from the host's skin.

* * * * *